United States Patent [19]
Dolynchuk et al.

[11] Patent Number: 5,885,982
[45] Date of Patent: Mar. 23, 1999

[54] USE OF TRANSGLUTAMINASE INHIBITOR FOR THE TREATMENT OF SCAR TISSUE

[76] Inventors: Kenneth Nicholis Dolynchuk; John Michael Bowness, both of University of Manitoba 770 Bannatyne Ave., Winnipeg, Manitoba, Canada, R3E 0W3

[21] Appl. No.: 845,117

[22] PCT Filed: Mar. 23, 1992

[86] PCT No.: PCT/CA92/00123

§ 371 Date: Nov. 14, 1994

§ 102(e) Date: Nov. 14, 1994

[87] PCT Pub. No.: WO93/18760

PCT Pub. Date: Sep. 30, 1993

Related U.S. Application Data

[63] Continuation of Ser. No. 307,621, Nov. 14, 1994, abandoned.

[51] Int. Cl.$^6$ .............................. A01N 43/00; C12Q 1/00; C12Q 1/52; A61K 31/74
[52] U.S. Cl. ......................... 514/210; 514/886; 514/871; 424/DIG. 78.06; 435/4; 435/16; 435/23; 435/24
[58] Field of Search ..................................... 514/210, 886, 514/871; 424/DIG. 78.06; 435/4, 16, 23, 24

[56] References Cited

U.S. PATENT DOCUMENTS

| | | | |
|---|---|---|---|
| 4,226,858 | 10/1980 | Pfirrmann et al. | 424/DIG. 13 |
| 4,428,939 | 1/1984 | Prockop | 424/177 |
| 4,444,787 | 4/1984 | Moorhead | 424/304 |
| 4,485,088 | 11/1984 | Chvapil | 424/304 |
| 4,507,321 | 3/1985 | Raisfeld | 424/326 |
| 4,618,490 | 10/1986 | De Marco | 424/DIG. 13 |
| 4,694,021 | 9/1987 | Schweiger | 514/949 |
| 4,929,630 | 5/1990 | Castelhano et al. | 514/380 |
| 4,946,870 | 8/1990 | Partain, III et al. | 514/777 |
| 4,968,713 | 11/1990 | Baldwin et al. | 514/398 |
| 4,970,297 | 11/1990 | Castelhano et al. | 530/331 |
| 4,997,854 | 3/1991 | Kagan et al. | 514/660 |
| 5,120,322 | 6/1992 | Davis et al. | 604/265 |
| 5,124,358 | 6/1992 | Kapil et al. | 514/603 |
| 5,132,119 | 7/1992 | Lee | 424/646 |
| 5,324,508 | 6/1994 | Adelstein et al. | 424/85.1 |
| 5,411,940 | 5/1995 | Nixon et al. | 514/12 |

FOREIGN PATENT DOCUMENTS

WO91/10427  7/1991  WIPO.

OTHER PUBLICATIONS

Annals of Surgery, vol. 193, No. 5, May 1981, E.E. Peacock; "Phamacologic Control of Surface Scarring in Human Beings", pp. 592–597.

Dolynchuk, Kenneth N; The Biochemistry of Wound Healing: The Characterization of a Wound Fucoprotein; Ph. D. Thesis; University of Manitoba (1986) pp. 1–128.

Dolynchuk, Kenneth N; The Biochemistry of Wound Healing: The Characterization and Assembly of a Wound Fucoprotein; vol. 48/11–B of Dissertation Abstracts International, p. 3271; 1987.

*Primary Examiner*—Louise N. Leary
*Attorney, Agent, or Firm*—Michael I. Stewart; Sim & McBurney

[57] ABSTRACT

A method of treating or preventing hypertrophic scar tissue in human skin comprising applying topically an effective amount of a non-toxic amine compound that is a transglutaminase inhibitor having a free amino group is disclosed. The amine compound that is a transglutaminase inhibitor is also selective for inhibiting Type III collagen peptide cross-linking.

9 Claims, 8 Drawing Sheets

USE OF TRANSGLUTAMINASE INHIBITOR FOR THE TREATMENT OF SCAR TISSUE

This application is a continuation of Ser. No. 08/307,621 filed Nov. 14, 1994 now abn. which is a 371 of PCT/CA92/00123 filed Mar. 23, 1992.

BACKGROUND OF THE INVENTION

The present invention relates to wound therapy, and in particular to the therapeutic treatment of hypertrophic scar tissue.

Scar tissue is formed during healing of wounds, caused for example by burn, traumatic injury and elective operative incisions. Often unpredictably, hypertrophy of the scar tissue occurs. Hypertrophic scar formation is characterized by the accumulation of collagen type III out of proportion to collagen type I.

Current procedures and materials for wound treatment include the use of compounds with potentially serious side effect, to highly invasive excisional procedures.

In accordance with one aspect of the invention, a composition for the therapeutic treatment of hypertrophic scar tissue is provided, comprising a non-toxic transglutaminase inhibitor having a free amino group, or a pharmaceutically acid addition salt thereof, and a pharmaceutically acceptable carrier or diluent.

According to another aspect of the invention, a method of treating hypertrophic scar tissue is also provided comprising applying to the scar tissue an effective amount of a non-toxic transglutaminase inhibitor having a free amino group, or a pharmaceutically acid addition salt acceptable acid addition salt thereof, and a pharmaceutically acceptable carrier or diluent.

Tranglutaminases are enzymes present in plasma and various tissues which form isopeptide bonds between reactive glutaminyl groups an the e-amino group of lysine in certain proteins. For example, type III procollogen has been shown to be a specific and avid substrate for transglutominase. During skin wound healing it appears that type III procollagen amino peptide (PIIP) is cross-linked to other components of the wound matrix, such as fibrin and fibronectin, by tissue tranglutominase. It is therefore hypothesized that if a transglutaminase inhibitor having a free amino group is introduced to the wound site, its free amino group will preferentially bind to the glutominyl group, and thus inhibit the intended protein substrated from cross-linking, forming an inert analog-amine adduct instead.

Known non-toxic transglutaminase inhibitors of this type include aminoacetonitrile,(dansyl) cadaverine (1,5-diaminopentane), spermidine and putrescine (1,4-diaminobutane). All of these compounds are non-toxic primary amines.

More specifically, aminoacetonitrile is a primary aliphatic lower-alkyl (C1-5) monoamine. Spermidine is a primary aliphatic aklylamine. Putrescine and (dansyl) cadaverine are primary aliphatic lower-alkyl (C1-5) polyamines. Other similar, non-toxic primary amines of these types are also contemplated.

It will be appreciated by those skilled in the art that the active compounds may be usefully applied in the form of pharmaceutically acceptable acid addition salts such as hydrochlorides and hydrogen sulfates.

The pharmaceutically acceptable carrier is typically a eutectic cream or ointment to facilitate spreading over the wound area. For topical application, mineral oil has been found particularly suitable. Other suitable carriers include polyethylene glycols.

For topical applications, the effective amount of the active compound is in the range of 25 to 100 mM. and preferably about 50 mM.

Once the composition is applied to the wound it may advantageously be occiuded with a dressing or incorporated into a transepidermal patch dressing.

It will be appreciated that, although the compositions according to the invention are particularly useful for topical application to external wounds, it is also to be expected to be of value in the treatment of internal scar tissue. In such cases, the composition may be applied by catheter infusion or by an implantable time release mechanism. One specific example is diffusion through the elastomer coating of a breast implant.

BRIEF DESCRIPTION OF DRAWINGS

FIGS. 1 to 9 are photographic illustrations of the effects of the compositions according to the invention on hypertrophic scar tissue in human patients.

DESCRIPTION OF THE PREFERRED EMBODIMENT

In the examples which follow, the active compound employed was putrescine. Putrescine was selected as it is naturally occurring, highly specific and readily available.

Putrescine (Sigma Chemical Co., St. Louis, Mo.) was compounded in a eutectic base (Glaxo Canada Ltd., Toronto, Ont.) at 0.8% (W/V) concentration (50 mM).

Patients applied the ointment daily and occluded the area with Duoderm $CGF_R$ or $Actiderm_R$ (Convatec, Princeton, N.J.). If removed for any reason the cream was to be reapplied as soon as possible. Patients were to report the presence of any reaction which developed.

All photographic documentation was carried out by the professional medical photography department using similar lighting and techniques for each wound at the various times recorded.

CASE 1

A 32-year old male having burns involving the trunk and lower extremities resulting from a motor vehicle accident was treated. Burn management consisted of excision and grafting of the lower extremities and a full take occurred in all areas except over the Achilles tendons bilaterally. The patient was discharged home with contractures of the right leg preventing full extension.

At a three-week follow-up, the patient was unchanged and gross hypertrophy of the right leg and, to a lesser extent, the left leg was apparent. The patient then was treated with the composition of the invention for one month to the right leg only. During this period, ulceration over tendon Achilles healed fully, but that over the left did not show signs of improvement despite treatment with dressings. The scars were less hypertrophic on the right leg.

At a three-month follow-up, the right knee had a full range of movement and signs of hypertrophy on the right had resolved, whereas the left side was still quite red and raised. The scars on the left also felt quite hard, even though pressure garments were continuously used.

Figure 1:
Figure 2:
Figure 3:
Figure 4:

FIGS. 1 to 4 are photographs of the patient. FIGS. 1 and 2 are side and posterior views of the patient prior to treatment while FIGS. 3 and 4 are side and posterior views of the patient post-treatment.

The results obtained in this case exemplify the utility of the compositions of the invention in treating early hypertrophy in burn patients, preventing the need for surgical release of contractures, and allowing stabilization of unhealed areas.

CASE 2

A 3-year old female with a scald burn sustained 9 months previously and treated by excision and grafting was treated. The patient had scar contractures which were fairly mature, had fixed deformities of the toes which prevented normal shoe wear, and was developing minor ulceration from her special footwear.

A composition according to the invention was applied for one month and the scars were seen to soften with improvement in the skin stability over that time period. At a three month follow-up, some residual deformity persisted but the patient had regained full range of motion and was again able to wear normal footwear.

Figure 5:
Figure 6:

FIGS. 5 and 6 are photographs of the patient. FIG. 5 being taken prior to treatment and FIG. 6 post-treatment. These results show the utility of the compositions of the invention in the treatment of mature burn scar tissue.

CASE 3

A 12-year old female was presented one year after an iliac crest free bone flap reconstruction for a dermatofibroma of the mandible resected 6 years previously. The patient had gross hypertrophy of her scars along the entire suture line. In the postauricular area, she had a keloid-like scar which caused protruding of the ear itself.

The scars were excised and the patient was treated with a composition of the invention for one month. Since the treatment, there has been no recurrence of hypertrophy in the excised areas. Further follow-up at 6 months reveals maturation of scars and quality similar to that seen typically in much older ones.

Figure 7:
Figure 8:

FIGS. 7 and 8 are photographs of the patient. FIG. 7 was taken pretreatment, while FIG. 8 was taken post-treatment. These results show the utility of the compositions of the invention in preventing hypertrophic scar tissue formation.

As seen in the first of three cases studied subsequently, skin stability is not adversely affected by topical putrescine. In fact, epithelialization occurs more rapidly in the presence of the composition of the invention.

The first patient (case 1) was assessed subsequently at two years post injury by the Workers Compensation Board physician who found a thirty percent greater range of motion on the treated right lower extremity as compared to the left. He had no evidence of hypertrophic scar contracture on the right at this time. However, there were obvious contractures on the left, which was initially the less severely injured extremity. This exemplifies the use of the composition of the invention in treating early hypertrophy in burn patients, preventing the need for surgical release of contractures and allowing stabilization of unhealed areas.

The second case (case 2) demonstrates the application to established contractures with reasonable improvement in appearance and function. It also exemplifies the use of the composition under a pressure garment.

The last example (case 3) is that of prophylactic use in a patient prone to hypertrophic scar formation. Overall wound healing was not adversely affected and hypertrophy was well controlled.

In no case did wounds undergoing treatment fail to heal normally aside from varying degrees of hypertrophy. Patients tolerated the composition well. In a previous uncontrolled study as well as in the present work virtually no side effects were witnessed. Out of a total of one hundred and fifteen patients treated, only one patient developed a rash which necessitated discontinuance of the treatment. He went on to require excision and grafting of his hypertrophic burn scars. No one else required further revision, being satisfied with the clinical improvement at one year post treatment.

A major advantage of the treatment according to the invention is the ease of use. A once daily application under an occlusive dressing is relatively convenient. Further advantages are the lack of associated morbidity seen with other treatment modulities such as the skin atrophy and painful injection from intralesional steroid treatment. Moreover, anaplasia as seen in irradiated scars is unlikely. It is also apparent that the composition may be readily applied beneath pressure garments.

We claim:

1. A method of treating or preventing hypertrophic scar tissue in humans, comprising applying to extracellular wound scar tissue in human skin an effective amount of a non-toxic amine compound having a free amino group, said amine compound being a transglutaminase inhibitor which is selective for inhibiting Type III collagen peptide cross-linking, or a pharmaceutically-acceptable acid addition salt of said amino compounds, in the form of a composition with a pharmaceutically-acceptable carrier or diluent and formulated for topical application to said extracellular wound.

2. A method according to claim 1, wherein the effective amount is 25 to 100 mM.

3. A method according to claim 2, wherein the effective amount is about 50 mM.

4. A method according to claim 1, wherein the amine compound is a primary amine.

5. A method according to claim 4, wherein the amine is a polyamine.

6. A method according to claim 5, wherein the amine is a C1–5 alkyl amine.

7. A method according to claim 6, wherein the amine is putrescine.

8. A method according to claim 7, wherein the carrier is a eutectic cream or ointment.

9. The method of claim 8 including the further step of occluding the wound with a dressing.

* * * * *